(12) United States Patent
Aharoni et al.

(10) Patent No.: US 7,918,886 B2
(45) Date of Patent: Apr. 5, 2011

(54) DOUBLE INSERTION INTRAOCULAR IMPLANT

(75) Inventors: Eli Aharoni, Tel Aviv (IL); Yossi Gross, Moshav Mazor (IL)

(73) Assignee: VisionCare Ophthalmic Technologies Inc., Saratoga, CA (US)

( * ) Notice: Subject to any disclaimer, the term of this patent is extended or adjusted under 35 U.S.C. 154(b) by 601 days.

(21) Appl. No.: 11/420,327

(22) Filed: May 25, 2006

(65) Prior Publication Data
US 2007/0276483 A1    Nov. 29, 2007

(51) Int. Cl.
*A61F 2/16* (2006.01)
(52) U.S. Cl. ...................... 623/6.34; 623/6.37
(58) Field of Classification Search .............. 623/6.11, 623/6.13, 6.14, 6.34, 6.37
See application file for complete search history.

(56) References Cited

U.S. PATENT DOCUMENTS

| | | | |
|---|---|---|---|
| 3,515,461 A | 6/1970 | Rayces et al. | |
| 4,056,855 A * | 11/1977 | Kelman | 623/6.38 |
| 4,074,368 A | 2/1978 | Levy, Jr. et al. | |
| 4,463,458 A * | 8/1984 | Seidner | 623/6.43 |
| 4,527,294 A | 7/1985 | Heslin | |
| 4,581,031 A | 4/1986 | Koziol et al. | |
| 4,596,578 A * | 6/1986 | Kelman | 623/6.17 |
| 4,666,446 A | 5/1987 | Koziol et al. | |
| 4,710,197 A | 12/1987 | Donn et al. | |
| 4,731,078 A * | 3/1988 | Stoy et al. | 623/6.13 |
| 4,743,254 A | 5/1988 | Davenport | |
| 4,833,890 A | 5/1989 | Kelman | |
| 4,892,543 A | 1/1990 | Turley | |
| 4,911,714 A | 3/1990 | Poley | |
| 4,911,715 A | 3/1990 | Kelman | |
| 4,955,902 A * | 9/1990 | Kelman | 623/6.54 |
| 5,026,396 A * | 6/1991 | Darin | 623/6.41 |
| 5,044,743 A | 9/1991 | Ting | |
| 5,108,429 A | 4/1992 | Wiley | |
| 5,222,981 A | 6/1993 | Werblin | |
| 5,354,335 A | 10/1994 | Lipshitz et al. | |
| 5,384,606 A | 1/1995 | Koch et al. | |
| 5,391,202 A | 2/1995 | Lipshitz et al. | |
| 5,405,387 A * | 4/1995 | Sodero | 623/6.13 |
| 5,628,798 A | 5/1997 | Eggleston et al. | |
| 5,653,751 A | 8/1997 | Samiy et al. | |
| 5,814,103 A | 9/1998 | Lipshitz et al. | |
| 5,876,442 A * | 3/1999 | Lipshitz et al. | 623/6.34 |

(Continued)

FOREIGN PATENT DOCUMENTS

DE    34 28 895 A1    2/1986

(Continued)

OTHER PUBLICATIONS

European Search Report dated May 28, 2004 re: Application No. EP 04 25 0124.

(Continued)

*Primary Examiner* — David Isabella
*Assistant Examiner* — Joshua Levine
(74) *Attorney, Agent, or Firm* — Fish & Richardson P.C.

(57) ABSTRACT

An intraocular telescopic lens assembly including a negative lens having a negative lens optical axis, a positive lens having a positive lens optical axis and a spacer disposed intermediate the negative lens and the positive lens, the spacer being operative to maintain mutual orientation of the negative lens and the positive lens such that the negative lens optical axis is coaxial with the positive lens optical axis.

17 Claims, 8 Drawing Sheets

U.S. PATENT DOCUMENTS

| | | | |
|---|---|---|---|
| 5,876,442 A | 3/1999 | Gross et al. | |
| 5,928,283 A | 7/1999 | Gross et al. | |
| 5,964,802 A | 10/1999 | Anello et al. | |
| 6,007,579 A | 12/1999 | Lipshitz et al. | |
| 6,066,171 A | 5/2000 | Lipshitz et al. | |
| 6,197,057 B1 | 3/2001 | Peyman et al. | |
| 6,358,280 B1 | 3/2002 | Herrick | |
| 6,400,989 B1 | 6/2002 | Eckmiller | |
| 6,569,199 B1 | 5/2003 | Dotan et al. | |
| 6,596,026 B1 | 7/2003 | Gross et al. | |
| 6,818,017 B1* | 11/2004 | Shu | 623/6.11 |
| 6,847,847 B2 | 1/2005 | Nisch et al. | |
| 6,849,090 B2* | 2/2005 | Nigam | 623/5.13 |
| 6,902,577 B2 | 6/2005 | Lipshitz et al. | |
| 6,913,620 B2 | 7/2005 | Lipshitz et al. | |
| 6,972,032 B2 | 12/2005 | Aharoni et al. | |
| 7,008,448 B2 | 3/2006 | Lipshitz et al. | |
| 7,079,900 B2 | 7/2006 | Greenburg et al. | |
| 7,276,080 B2 | 10/2007 | Murakami et al. | |
| 2002/0101564 A1* | 8/2002 | Herrick | 351/161 |
| 2002/0143395 A1* | 10/2002 | Skottun | 623/6.34 |
| 2002/0173846 A1* | 11/2002 | Blake et al. | 623/6.18 |
| 2003/0060881 A1* | 3/2003 | Glick et al. | 623/6.37 |
| 2003/0078656 A1* | 4/2003 | Nguyen | 623/6.37 |
| 2003/0105522 A1* | 6/2003 | Glazier | 623/6.13 |
| 2003/0187502 A1 | 10/2003 | Lipshitz | |
| 2003/0187503 A1 | 10/2003 | Lipshitz et al. | |
| 2003/0204256 A1* | 10/2003 | Peng et al. | 623/6.34 |
| 2004/0117011 A1 | 6/2004 | Aharoni et al. | |
| 2004/0148022 A1* | 7/2004 | Eggleston | 623/6.22 |
| 2004/0181279 A1 | 9/2004 | Nun | |
| 2005/0071002 A1* | 3/2005 | Glazier | 623/6.13 |
| 2006/0004446 A1 | 1/2006 | Aharoni et al. | |

FOREIGN PATENT DOCUMENTS

| | | | |
|---|---|---|---|
| DE | 195 01 444 A1 | | 7/1996 |
| EP | 0 099 641 | | 2/1984 |
| EP | 0162573 | | 11/1985 |
| EP | 0 897 702 A2 | | 2/1999 |
| EP | 1475055 | | 11/2004 |
| FR | 2666735 | | 3/1992 |
| FR | 2666735 A1 | * | 3/1992 |
| GB | 1303579 | | 1/1973 |
| WO | WO-83/01566 A1 | | 5/1983 |
| WO | WO-88/06430 | | 9/1988 |
| WO | WO-94/07435 A1 | | 4/1994 |
| WO | WO-0004849 | | 2/2000 |
| WO | WO-00/38593 A1 | | 7/2000 |

OTHER PUBLICATIONS

An Office Action dated Jan. 20, 2009, which issued during the prosecution of Applicant's Japanese Patent Application No. 2004-7118.

An International Search Report dated Feb. 26, 2007, which issued during the prosecution of Applicant's PCT Patent Application No. PCT/IL06/00873.

An Office Action dated Aug. 29, 2009, which issued during the prosecution of Applicant's Canadian Patent Application No. 2,455,076.

An Office Action dated Sep. 8, 2009, which issued during the prosecution of Applicant's Japanese Patent Application No. 2004-560169.

An Office Action dated Sep. 9, 2009, which issued during the prosecution of Applicant's U.S. Appl. No. 11/069,581.

* cited by examiner

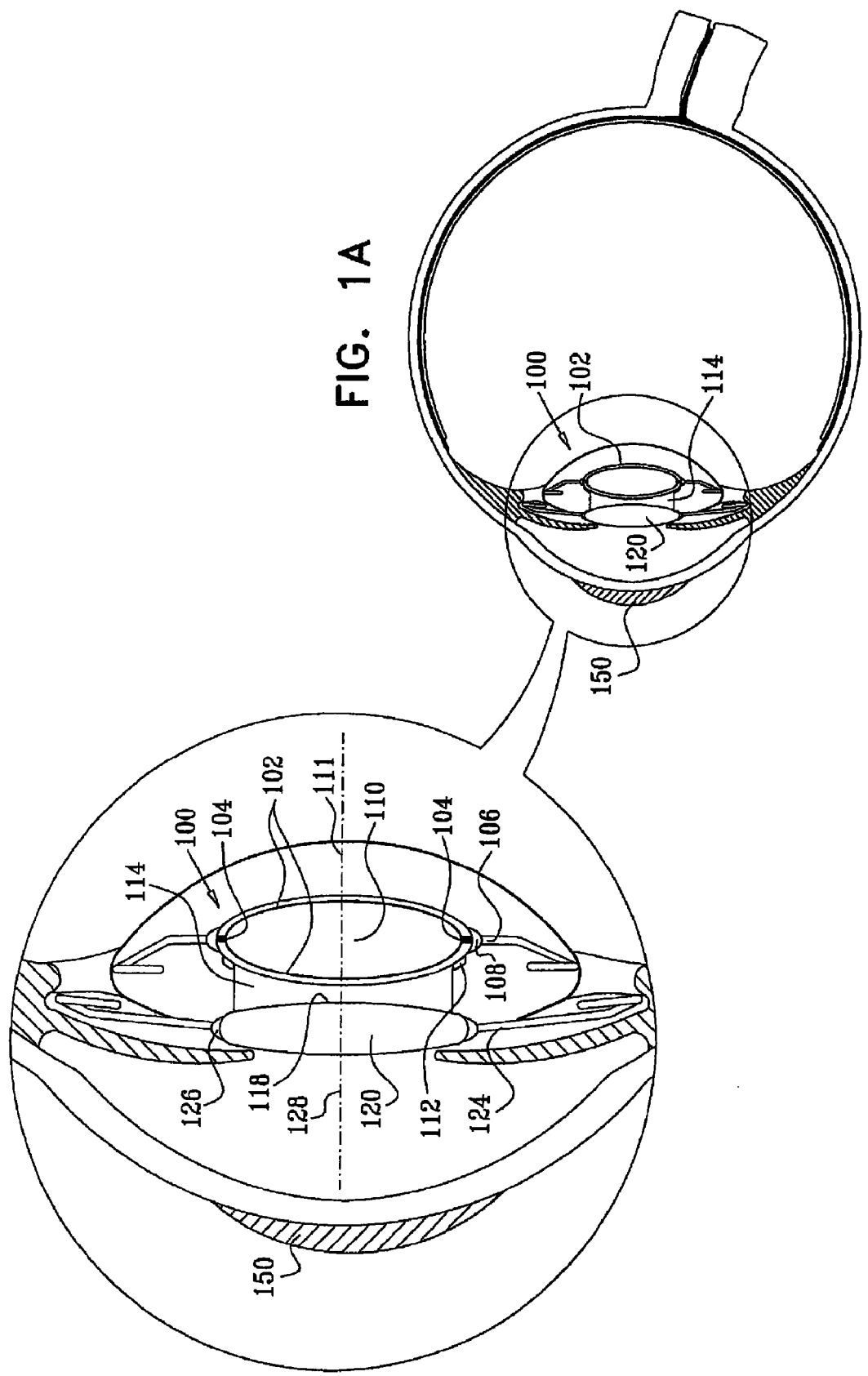

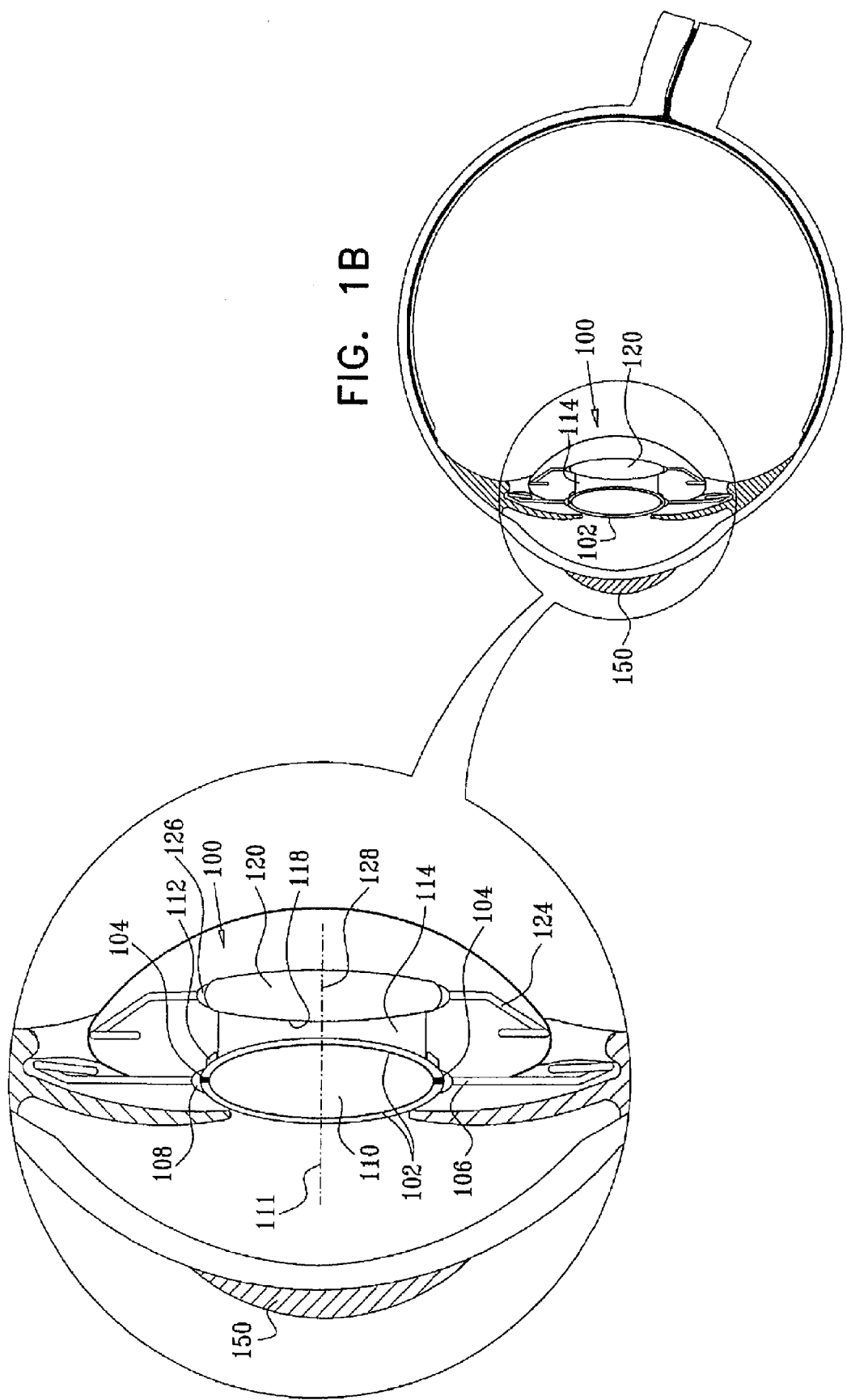

DOUBLE INSERTION INTRAOCULAR IMPLANT

FIELD OF THE INVENTION

The present invention relates to optical implants generally and more particularly to flat telescope intraocular lens implants.

BACKGROUND OF THE INVENTION

The following patent publications of the inventor/assignee are believed to represent the current state of the art:
U.S. Pat. Nos. 5,814,103; 5,876,442; 5,928,283; 6,007,579 and 6,066,171.

SUMMARY OF THE INVENTION

The present invention seeks to provide a flat telescope intraocular lens implant suitable for at least partially alleviating the symptoms characteristic of Age-related Macular Degeneration (AMD) and other maculopathy problems.

There is thus provided in accordance with a preferred embodiment of the present invention an intraocular telescopic lens assembly including a negative lens having a negative lens optical axis, a positive lens having a positive lens optical axis and a spacer disposed intermediate the negative lens and the positive lens, the spacer being operative to maintain mutual orientation of the negative lens and the positive lens such that the negative lens optical axis is coaxial with the positive lens optical axis.

In accordance with a preferred embodiment of the present invention the spacer is operative to maintain a predetermined minimum distance between the negative lens and the positive lens.

In accordance with another preferred embodiment of the present invention the spacer includes an additional lens. Preferably, the additional lens includes a negative lens.

In accordance with yet another preferred embodiment of the present invention the negative lens includes a first lens having a first circumference and a second lens having a second circumference, the first lens being fused together with the second lens along the first and second circumferences such that a gap is formed intermediate the first lens and the second lens. Preferably, the gap is maintained by vacuum. Alternatively, the gap is filled with gas.

In accordance with a further preferred embodiment of the present invention at least one of the first lens and the second lens has zero optical power. Preferably, the gap is sealed off from an exterior of the negative lens.

In accordance with yet a further preferred embodiment of the present invention the intraocular telescopic lens assembly also includes first haptics connected to the negative lens and second haptics connected to the positive lens, the first and second haptics being operative to maintain a predetermined maximum distance between the negative lens and the positive lens.

In accordance with an additional preferred embodiment of the present invention a predetermined maximum distance between the negative lens and the positive lens is maintained by snap-fit engagement between the spacer and the negative lens or between the spacer and the positive lens.

In accordance with another preferred embodiment of the present invention the intraocular telescopic lens assembly also includes a support element, mounted onto one of the negative lens and the positive lens, which supports at least a portion of the spacer. Preferably, the support element is ring shaped.

In accordance with yet another preferred embodiment of the present invention at least one of the positive lens and the negative lens includes a refractive optical element. Additionally or alternatively, at least one of the positive lens and the negative lens includes a diffractive optical element. Preferably, at least one of the positive lens and the negative lens is coated with an optical coating.

BRIEF DESCRIPTION OF THE DRAWINGS

The present invention will be understood and appreciated more fully from the following detailed description, taken in conjunction with the drawings in which:

FIGS. 1A and 1B are simplified illustrations of a doublet telescopic implant constructed and operative in accordance with a preferred embodiment of the present invention, implanted in the eye of a wearer wearing contact lenses in two alternative operative orientations;

DETAILED DESCRIPTION OF PREFERRED EMBODIMENTS

Figure 2A:
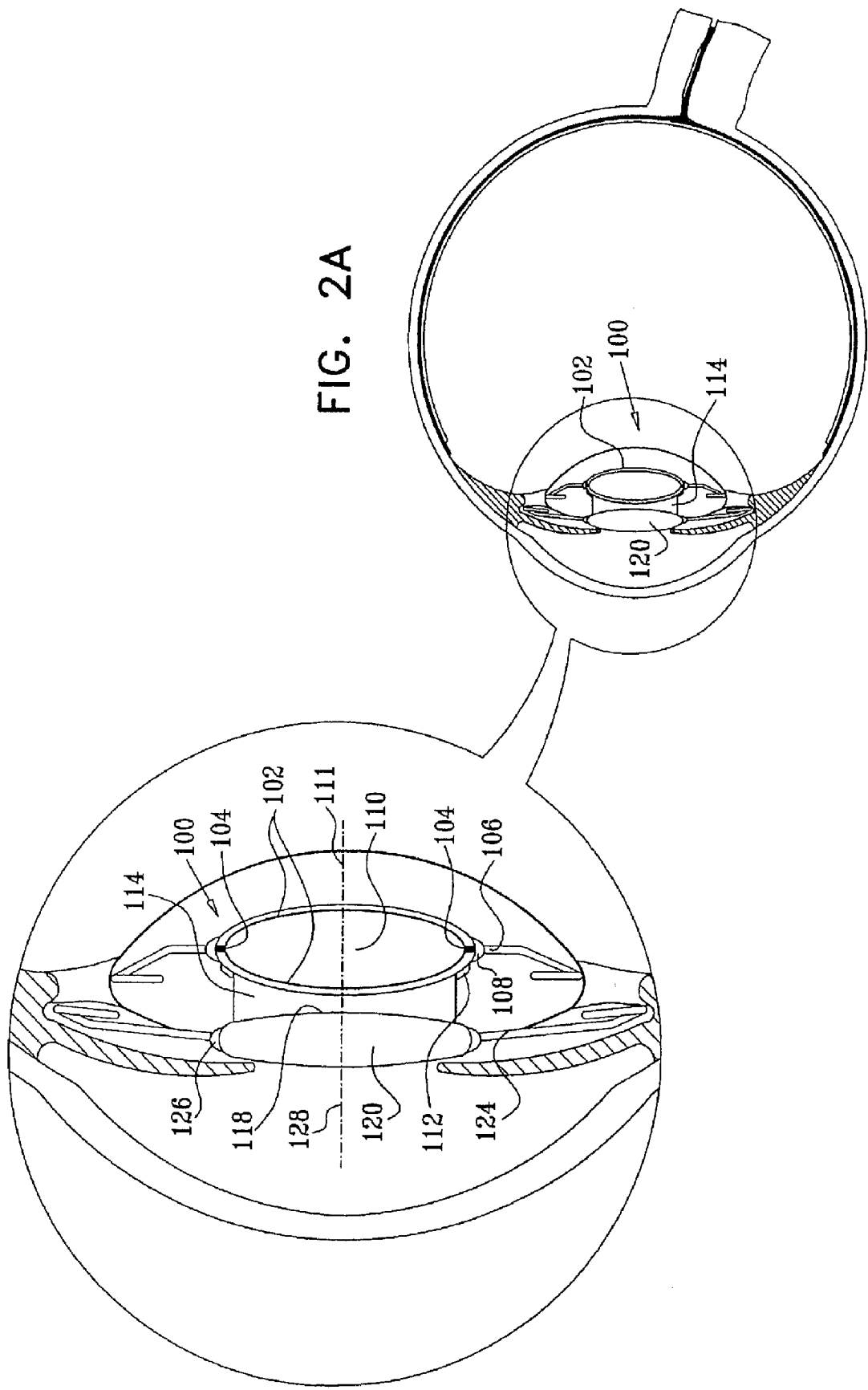
FIGS. 2A and 2B are simplified illustrations of the doublet telescopic implant of FIGS. 1A and 1B implanted in the eye of a wearer not wearing glasses or contact lenses in two alternative operative orientations.
Figure 2B:
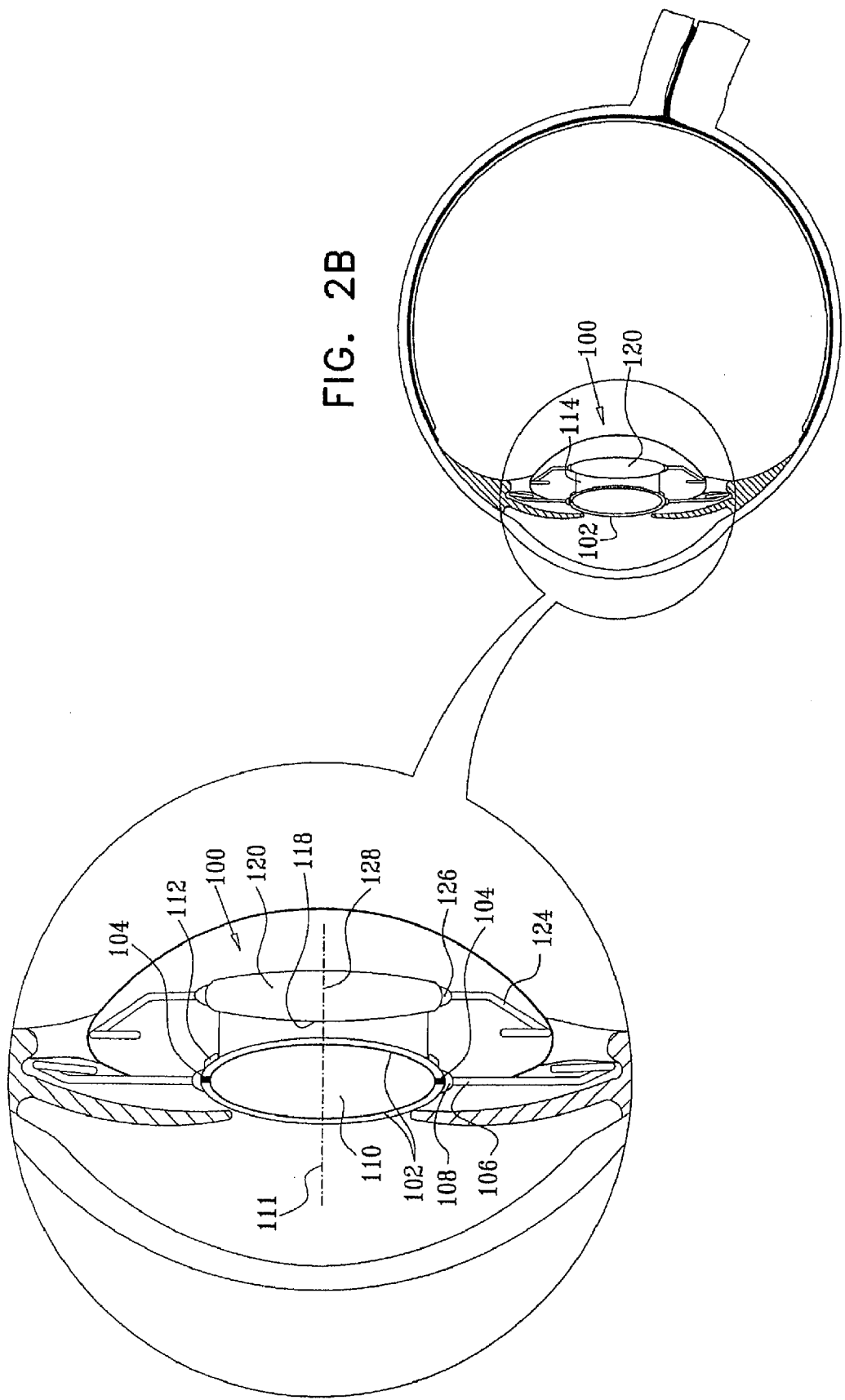

Reference is now made to FIGS. 1A and 1B, which are simplified illustrations of a doublet telescopic implant constructed and operative in accordance with a preferred embodiment of the present invention, implanted in the eye of a wearer wearing contact lenses in two alternative operative orientations and to FIGS. 2A and 2B, which are simplified illustrations of the doublet telescopic implant of FIGS. 1A and 1B implanted in the eye of a wearer not wearing glasses or contact lenses in two alternative operative orientations.

In accordance with a preferred embodiment of the present invention there is provided an intraocular telescopic lens assembly comprising a negative lens having a negative lens optical axis, a positive lens having a positive lens optical axis and a spacer disposed intermediate the negative lens and the positive lens, the spacer being operative to maintain mutual orientation of the negative lens and the positive lens such that the negative lens optical axis is coaxial with the positive lens optical axis.

As seen in FIGS. 1A and 1B, a doublet telescopic implant 100 preferably comprises a pair of lenses 102 which are fused together along respective circumferences 104 thereof, and have connected thereto haptics 106 via a haptics mounting structure 108.

It is an important feature of the present invention that a gap, which may be maintained under vacuum or filled with air or any other suitable gas, and which is designated by reference numeral 110, is formed intermediate the pair of lenses 102 and is operative to enhance refraction thereby. It is also an important feature of the present invention that the gap 110, which comprises the interior of the pair of lenses 102, is sealed from the exterior thereof, so as to prevent liquids or vapors from entering the implant.

It is appreciated that due to the gap 110 and the liquid environment surrounding the implant 100 when implanted in the eye, the pair of lenses 102 functions as a negative lens. The negative lens formed by lenses 102 preferably has a negative lens optical axis, indicated by reference numeral 111.

It is appreciated that in an alternative embodiment, the pair of lenses 102 may be replaced by positive lens having a gap formed therein using any suitable mechanism, and thus functioning as a negative lens.

Fixed to one of lenses 102 is a ring shaped support element 112, operative to receive and support a spacer 114 which is preferably formed of a lens, which is preferably a negative lens. A portion of the spacer 114 preferably is located at least partially within the ring shaped support element 112.

Disposed adjacent a surface 118 of spacer 114, and preferably in engagement therewith, is an additional lens 120, which is preferably a positive lens. Positive lens 120 has haptics 124 connected thereto via a haptic mounting structure 126, and includes a positive lens optical axis, indicated by reference numeral 128.

It is a particular feature of the present invention that spacer 114 is operative to maintain mutual orientation of the negative lens formed of lenses 102 and the positive lens 120 such that the negative lens optical axis 111 is coaxial with the positive lens optical axis 128. Spacer 114 is additionally operative to maintain a predetermined minimum distance between the negative lens formed of lenses 102 and the positive lens 120. The fixed distance between the negative lens formed of lenses 102 and the positive lens 120 is maintained by haptics 106 and 124 which push lenses 102 and 120 together generally against each other. Alternatively, the fixed distance between the negative lens formed of lenses 102 and the positive lens 120 may be maintained by snap fit engagement between one of the lenses 102 and 120 and the spacer 114.

Preferably, the lenses 102 and the additional lens 120 include refractive and diffractive optical elements.

Typically, the lenses 102 and the lens 120 are coated with optical coatings.

Turning specifically to FIG. 1A, it is seen that the doublet telescopic implant 100 is implanted in the wearer's eye such that the lenses 102 face a posterior portion of the eye. When the implant 100 is implanted in this orientation, the haptics 106 of the implant 100 are preferably shorter than the haptics 124. In this orientation, the doublet telescopic implant 100 at least partially alleviates the symptoms characteristic of Age-related Macular Degeneration (AMD) and other maculopathy problems.

Turning now to FIG. 1B, which illustrates an alternative operative orientation of the doublet telescopic implant 100 implanted in the eye of a wearer wearing contact lenses, it is seen that the doublet telescopic implant 100 is implanted in the wearer's eye such that the lenses 102 face an anterior portion of the eye. When the implant 100 is implanted in this orientation, the haptics 106 of the implant 100 are preferably longer than the haptics 124. In this orientation, the doublet telescopic implant 100 at least partially alleviates the tunnel vision symptom characteristic of glaucoma and retinosis pigmentosa.

It is appreciated that a contact lens 150 may enhance the functionality of the doublet telescopic implant 100, by further broadening the field of view of the user, and thus further alleviating the tunnel vision symptom.

Reference is now made to FIGS. 2A and 2B, which are simplified illustrations of the doublet telescopic implant 100 implanted in the eye of a wearer not wearing glasses or contact lenses in two alternative operative orientations.

FIG. 2A illustrates the doublet telescopic implant 100 implanted in the wearer's eye such that the lenses 102 face a posterior portion of the eye. When the implant 100 is implanted in this orientation, the haptics 106 of the implant 100 are preferably shorter than the haptics 124. In this orientation, the doublet telescopic implant 100 at least partially alleviates the symptoms characteristic of Age-related Macular Degeneration (AMD) and other maculopathy problems.

FIG. 2B illustrates an alternative operative orientation of the doublet telescopic implant 100 implanted in the eye of a wearer not wearing glasses or contact lenses. As seen in FIG. 2B, the doublet telescopic implant 100 implanted in the wearer's eye such that the lenses 102 face an anterior portion of the eye. When the implant 100 is implanted in this orientation, the haptics 106 of the implant 100 are preferably longer than the haptics 124. In this orientation, the doublet telescopic implant 100 at least partially alleviates the tunnel vision symptom characteristic of glaucoma and retinosis pigmentosa.

It is appreciated that an additional lens (not shown) may be placed in the anterior chamber of the eye, and may cooperate with the doublet telescopic implant 100 in alleviating symptoms characteristic of Age-related Macular Degeneration, glaucoma or retinosis pigmentosa. The additional lens may be a positive lens, a negative lens or any other suitable lens.

Figure 3A:
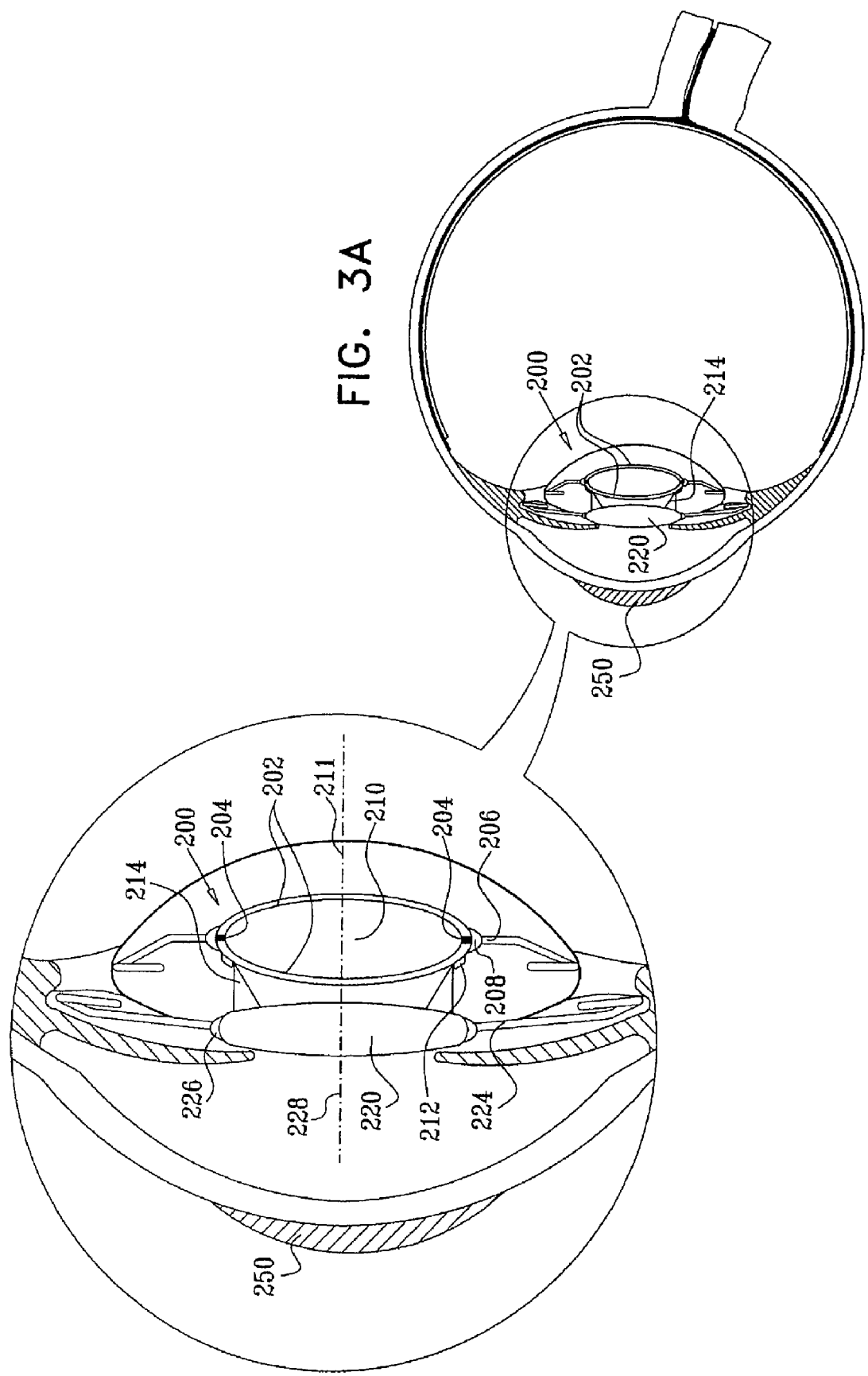
FIGS. 3A and 3B are simplified illustrations of a doublet telescopic implant constructed and operative in accordance with another preferred embodiment of the present invention, implanted in the eye of a wearer wearing contact lenses in two alternative operative orientations.
Figure 3B:
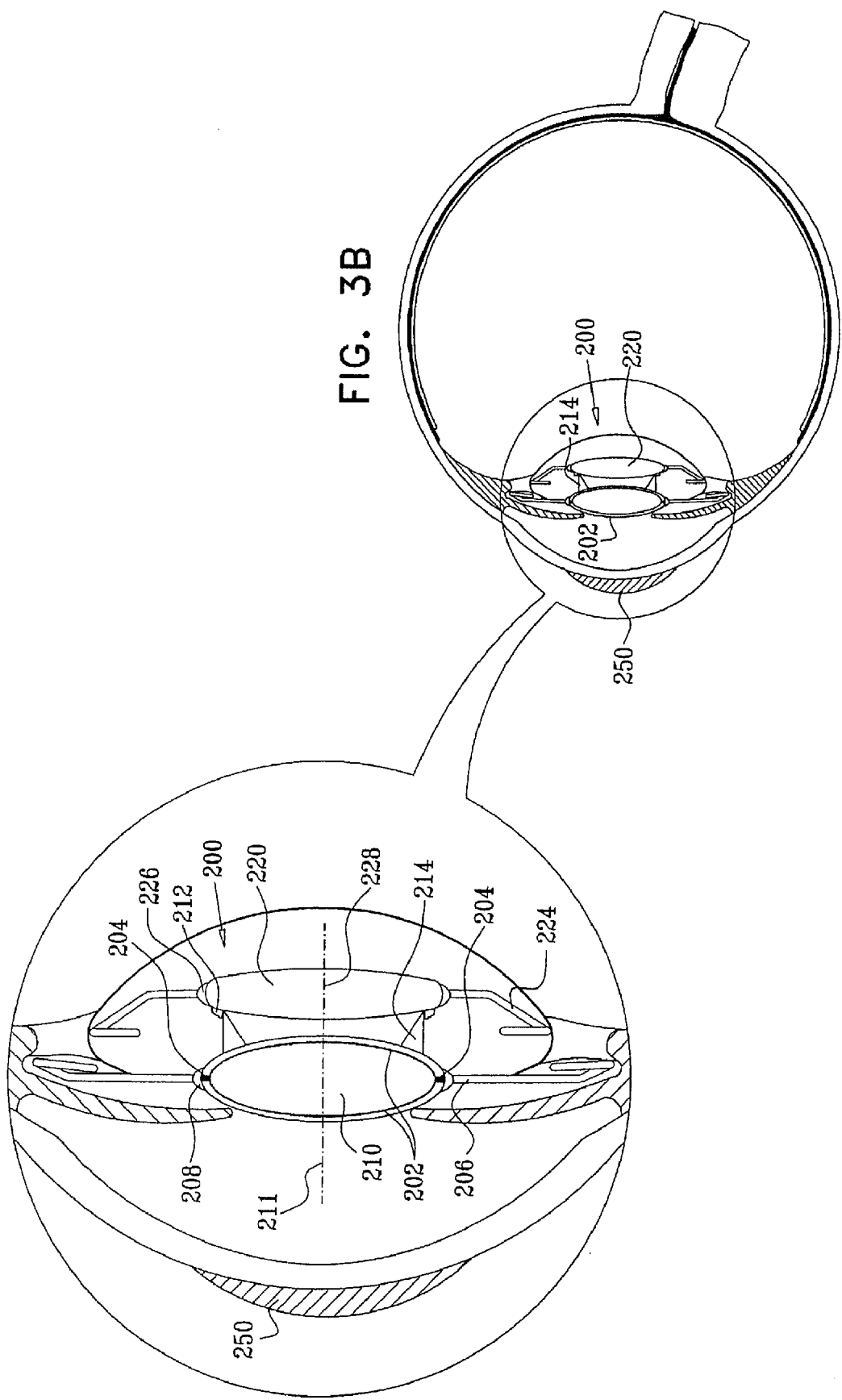
Figure 4A:
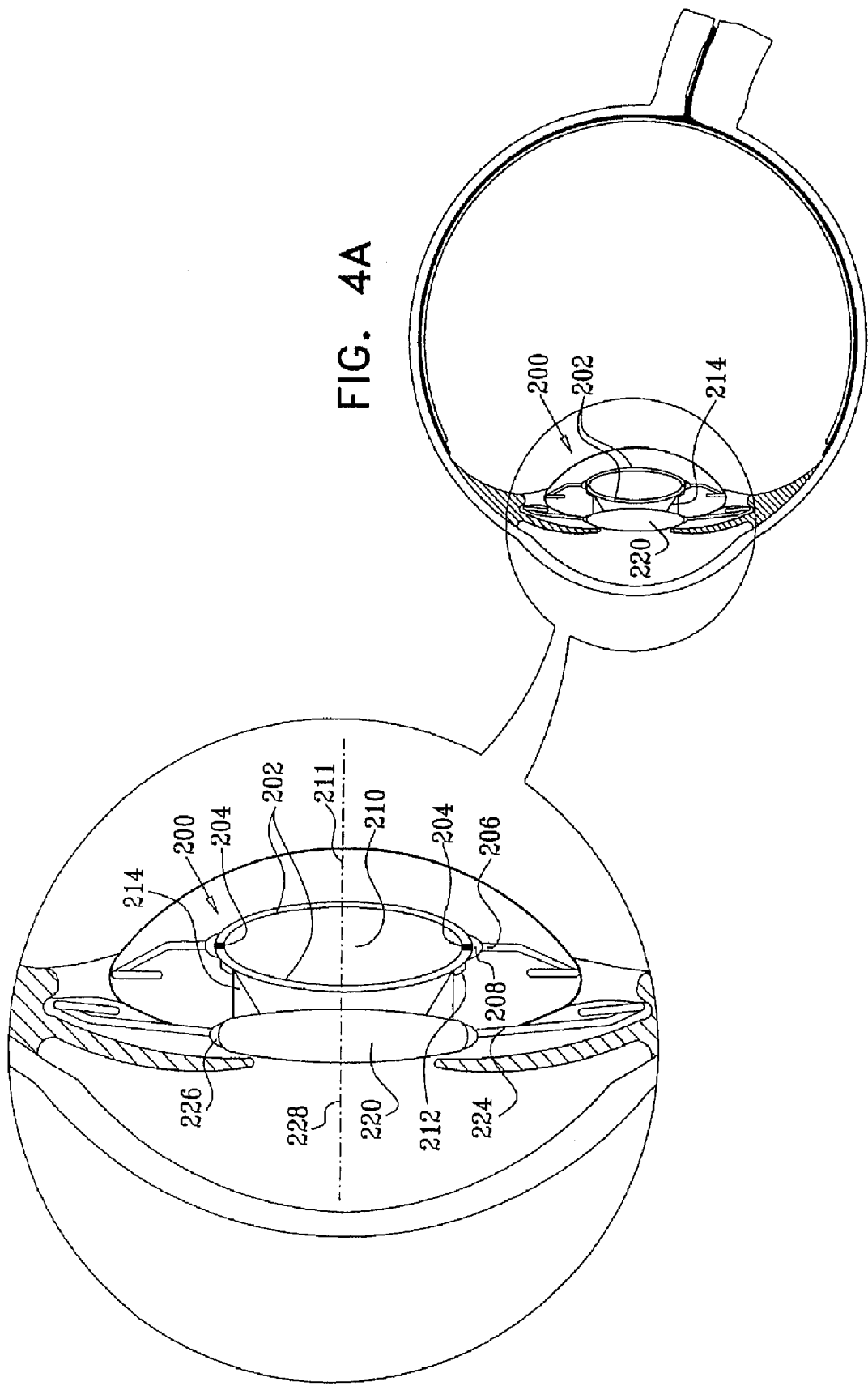
FIGS. 4A and 4B are simplified illustrations of the doublet telescopic implant of FIGS. 3A and 3B implanted in the eye of a wearer not wearing glasses or contact lenses in two alternative operative orientations.
Figure 4B:
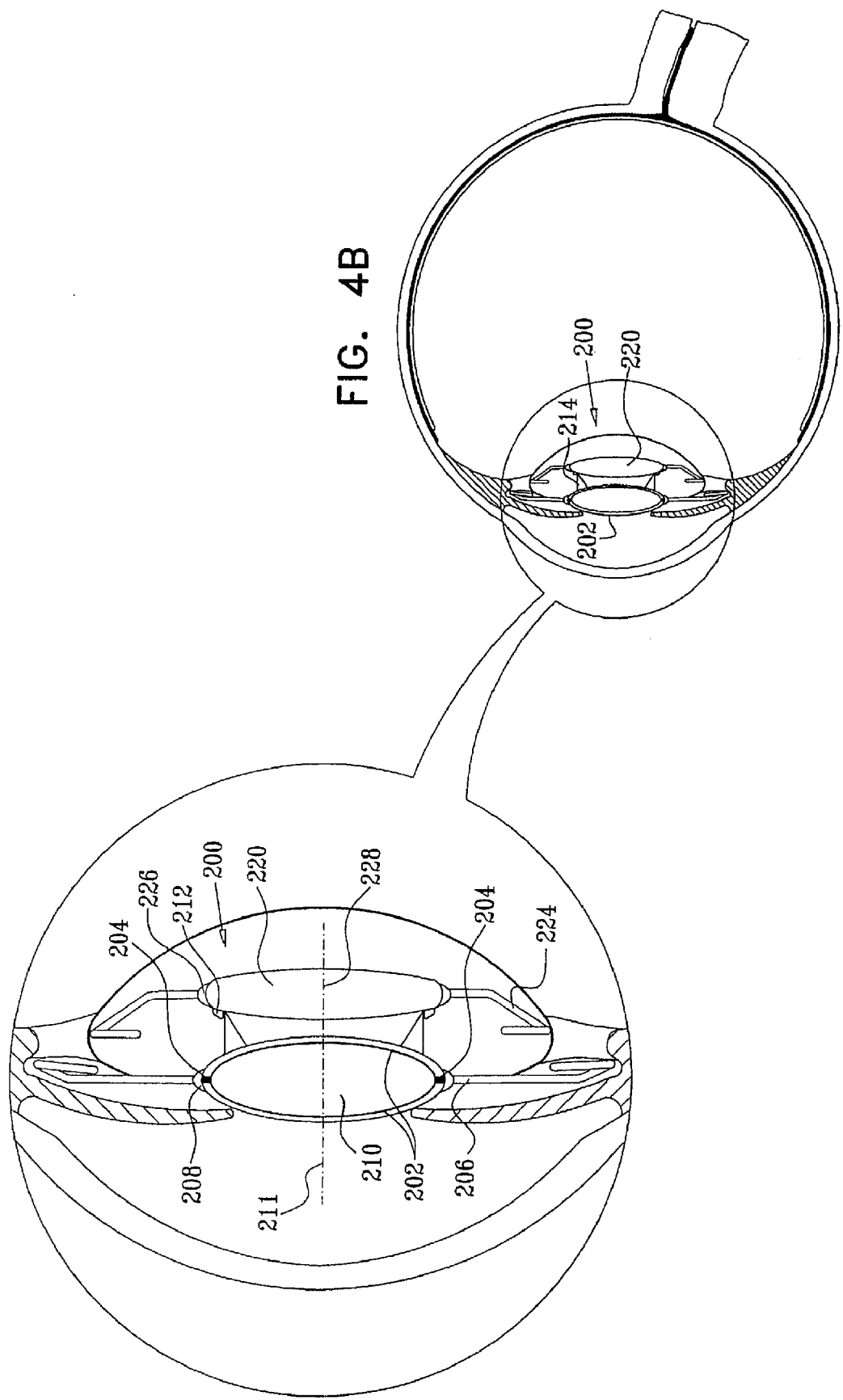

Reference is now made to FIGS. 3A and 3B, which are simplified illustrations of a doublet telescopic implant constructed and operative in accordance with another preferred embodiment of the present invention, implanted in the eye of a wearer wearing contact lenses in two alternative operative orientations and to FIGS. 4A and 4B, which are simplified illustrations of the doublet telescopic implant of FIGS. 3A and 3B implanted in the eye of a wearer not wearing glasses or contact lenses in two alternative operative orientations.

As seen in FIGS. 3A and 3B, a doublet telescopic implant 200 preferably comprises a pair of lenses 202, which are fused together along respective circumferences 204 thereof, and have connected thereto haptics 206 via a haptics mounting structure 208.

It is an important feature of the present invention that a gap, which may be maintained under vacuum or filled with air or any other suitable gas, and which is designated by reference numeral 210, is formed intermediate the pair of lenses 202 and is operative to enhance refraction thereby. It is also an important feature that the gap 210, which comprises the interior of the pair of lenses 202, is sealed from the exterior thereof, so as to prevent liquids or vapors from entering the implant. It is appreciated that due to the gap 210 and the liquid environment surrounding the implant 200 when implanted in the eye, the pair of lenses 202 functions as a negative lens. The negative lens formed by lenses 202 preferably has a negative lens optical axis, indicated by reference numeral 211.

It is appreciated that the gap 210, defining the negative nature of the lens formed of lenses 202, may alternatively be formed in a positive lens using any suitable mechanism. In such a case the positive lens including the gap would replace the pair of lenses 202.

As shown in FIGS. 3A and 4A, fixed to one of lenses 202 is a ring shaped support element 212, operative to receive and support a spacer 214, which is preferably ring shaped, but may alternatively be formed in any other suitable way. The spacer 214 is preferably fixed to an additional lens 220, which is preferably a positive lens. Lens 220 has haptics 224 connected thereto via a haptic mounting structure 226, and includes a positive lens optical axis, indicated by reference numeral 228.

Alternatively, as shown in FIGS. 3B and 4B, spacer 214 may be fixed to one of lenses 202 and support element 212 may be fixed to lens 220.

It is a particular feature of the present invention that spacer 214 is operative to maintain mutual orientation of the negative lens formed of lenses 202 and the positive lens 220 such that the negative lens optical axis 211 is coaxial with the positive lens optical axis 228. Spacer 214 is additionally operative to maintain a predetermined minimum distance between the negative lens formed of lenses 202 and the positive lens 220. The fixed distance between the negative lens formed of lenses 202 and the positive lens 220 is maintained by haptics 206 and 224 which push lenses 202 and 220 together generally against each other. Alternatively, the fixed distance between the negative lens formed of lenses 202 and the positive lens 220 may be maintained by snap fit engagement between one of lenses 202 and 220 and the spacer 214.

Preferably, the lenses 202 and the lens 220 include refractive and diffractive optical elements.

Typically, the lenses 202 and the lens 220 are coated with optical coatings.

Turning specifically to FIG. 3A, it is seen that the doublet telescopic implant 200 is implanted in the wearer's eye such that the lenses 202 face a posterior portion of the eye. When the implant 200 is implanted in this orientation, the haptics 206 of the implant 200 are preferably shorter than the haptics 224. In this orientation, the doublet telescopic implant 200 at least partially alleviates the symptoms characteristic of Age-related Macular Degeneration (AMD) and other maculopathy problems.

Turning now to FIG. 3B, which illustrates an alternative operative orientation of the doublet telescopic implant 100 implanted in the eye of a wearer wearing contact lenses, it is seen that doublet telescopic implant 200 is implanted in the wearer's eye such that the lenses 202 face an anterior portion of the eye. When the implant 200 is implanted in this orientation, the haptics 206 of the implant 200 are preferably longer than the haptics 224. As described hereinabove, when the implant 200 is implanted in this orientation, the ring shaped support element 212 is fixed to lens 220 and the spacer 214 is fixed to lens 202, and is located partially within support element 212. In this orientation, the doublet telescopic implant 100 at least partially alleviates the tunnel vision symptom characteristic of glaucoma and retinosis pigmentosa.

It is appreciated that a contact lens 250 may enhance the functionality of the doublet telescopic implant 200, by further broadening the field of view of the wearer thereof, and thus further alleviating the tunnel vision symptom.

Reference is now made to FIGS. 4A and 4B, which are simplified illustrations of the doublet telescopic implant 200 implanted in the eye of a wearer not wearing glasses or contact lenses in two alternative operative orientations.

FIG. 4A illustrates the doublet telescopic implant 200 implanted in the wearer's eye such that the lenses 202 face a posterior portion of the eye. When the implant 200 is implanted in this orientation, the haptics 206 of the implant 200 are preferably shorter than the haptics 224. In this orientation, the doublet telescopic implant 200 at least partially alleviates the symptoms characteristic of Age-related Macular Degeneration (AMD) and other maculopathy problems.

FIG. 4B illustrates an alternative operative orientation of the doublet telescopic implant 100 implanted in the eye of a wearer not wearing glasses or contact lenses. As seen in FIG. 4B, the doublet telescopic implant 200 implanted in the wearer's eye such that the lenses 202 face an anterior portion of the eye. When the implant 200 is implanted in this orientation, the haptics 206 of the implant 200 are preferably longer than the haptics 224. As described hereinabove, when the implant 200 is implanted in this orientation, the ring shaped support element 212 is fixed to lens 220 and the spacer 214 is fixed to lens 202, and is disposed partially within support element 212. In this orientation, the doublet telescopic implant 200 at least partially alleviates the tunnel vision symptom characteristic of glaucoma and retinosis pigmentosa.

It is appreciated that an additional lens (not shown) may be placed in the anterior chamber of the eye, and may cooperate with the doublet telescopic implant 200 in alleviating symptoms characteristic of Age-related Macular Degeneration, glaucoma or retinosis pigmentosa. The additional lens may be a positive lens, a negative lens or any other suitable lens.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specification and which are not in the prior art.

The invention claimed is:

1. An intraocular telescopic lens assembly comprising:
   a negative lens having a negative lens optical axis, said negative lens comprising a first lens having a first circumference and a second lens having a second circumference, said first lens being fused together with said second lens along said first and second circumferences such that a gap is formed intermediate said first lens and said second lens, said gap being filled with gas;
   a positive lens having a positive lens optical axis;
   a first pair of haptics connected to said negative lens;
   a second pair of haptics connected to said positive lens and different in length from said first pair of haptics connected to said negative lens, one pair of said first and second pairs of haptics being haptics of relatively greater length being configured for mounting in the sulcus of an eye and the other pair of said first and second pairs of haptics being haptics of relatively lesser length being configured for mounting in the bag of the eye; and
   a spacer disposed intermediate said negative lens and said positive lens, said spacer being operative to maintain mutual orientation of said negative lens and said positive lens such that said negative lens optical axis is coaxial with said positive lens optical axis.

2. An intraocular telescopic lens assembly according to claim 1 and wherein said spacer is operative to maintain a predetermined minimum distance between said negative lens and said positive lens.

3. An intraocular telescopic lens assembly according to claim 1, and wherein said spacer comprises an additional lens.

4. An intraocular telescopic lens assembly according to claim 3 and wherein said additional lens comprises a negative lens.

5. An intraocular telescopic lens assembly according to claim 1 and wherein at least one of said first lens and said second lens has zero optical power.

6. An intraocular telescopic lens assembly according to claim 1 and wherein said gap is sealed off from an exterior of said negative lens.

7. An intraocular telescopic lens assembly according to claim 1 and wherein said first pair of haptics and said second pair of haptics are operative to maintain a predetermined maximum distance between said negative lens and said positive lens.

8. An intraocular telescopic lens assembly according to claim 1, and wherein a predetermined maximum distance between said negative lens and said positive lens is maintained by snap-fit engagement between said spacer and said negative lens.

9. An intraocular telescopic lens assembly according to claim 1, and wherein a predetermined maximum distance between said negative lens and said positive lens is maintained by snap-fit engagement between said spacer and said positive lens.

10. An intraocular telescopic lens assembly according to claim 1 and also comprising a support element, mounted onto one of said negative lens and said positive lens, which supports at least a portion of said spacer.

11. An intraocular telescopic lens assembly according to claim 10 and wherein said support element is ring shaped.

12. An intraocular telescopic lens assembly according to claim 1 and wherein at least one of said positive lens and said negative lens includes a refractive optical element.

13. An intraocular telescopic lens assembly according to claim 1 and wherein at least one of said positive lens and said negative lens includes a diffractive optical element.

14. An intraocular telescopic lens assembly according to claim 1 and wherein at least one of said positive lens and said negative lens is coated with an optical coating.

15. An intraocular telescopic lens assembly according to claim 1 and wherein said first pair of haptics are connected to said negative lens via a first mounting structure and said second pair of haptics are connected to said positive lens via a second mounting structure.

16. An intraocular telescopic lens assembly according to claim 15 and wherein said first pair of haptics engage said first mounting structure and do not engage said second mounting structure.

17. An intraocular telescopic lens assembly according to claim 1 and wherein said negative lens and said positive lens form a doublet.

* * * * *